United States Patent [19]

Pirio et al.

[11] Patent Number: 4,551,275

[45] Date of Patent: Nov. 5, 1985

[54] DESMETHYLIMIPRAMINE DERIVATIVES AND POLY(AMINO ACID) CONJUGATES

[75] Inventors: Marcel R. Pirio, San Jose; Prithipal Singh, Sunnyvale, both of Calif.

[73] Assignee: Syntex (U.S.A.) Inc., Palo Alto, Calif.

[21] Appl. No.: 592,492

[22] Filed: Mar. 23, 1984

[51] Int. Cl.[4] .................................................. C07G 7/00
[52] U.S. Cl. .............................. 260/239 D; 260/112 B; 260/121; 435/188
[58] Field of Search ............... 260/112 B, 121, 239 D; 435/188

[56] References Cited

U.S. PATENT DOCUMENTS 4,275,160  6/1981  Singh ................................... 260/121

*Primary Examiner*—Paul R. Michl
*Attorney, Agent, or Firm*—Theodore J. Leitereg; Bertram I. Rowland

[57] ABSTRACT

Desmethylimipramine functionalized compounds are provided for conjugation to antigenic compounds, particularly poly(amino acids) and enzymes. The antigenic conjugates are employed for the production of antibodies, which find particular use in immunoassays for the determination of desmethylimipramine, while the enzyme conjugate finds use in an enzyme assay for the determination of desmethylimipramine.

19 Claims, No Drawings

DESMETHYLIMIPRAMINE DERIVATIVES AND POLY(AMINO ACID) CONJUGATES

BACKGROUND OF THE INVENTION

1. Field of the Invention

Desmethylimipramine (a dibenzazepine derivative also referred to as desipramine) finds extensive use for the treatment of depression. In administering desmethylimipramine, it is frequently necessary to ensure that the desmethylimipramine blood level remains within a certain narrow concentration range, in order to insure effective dosage, while avoiding levels which may be toxic or produce undesirable effects.

It is desirable to provide a simple and rapid procedure for determining desmethylimipramine levels in serum or other physiological fluids, which provides reproducible values and is specific for the compound(s) of interest.

2. Brief Description of the Prior Art

Desmethylimipramine is closely related chemically to imipramine, amitriptyline and nortriptyline. Techniques reported for the determination of amitriptyline in biological fluids include the use of thin layer chromatography, gas-liquid chromatography (GLC) and GLC-mass spectrometry. Gilford, et al., *J. of Chrom.*, 105, 107–113 (1975); Gupta, et al., *Clin. Biochem.*, 9, 3 247–51 (1976); Nyberg and Martensson, *J. Chrom.*, 143, 491 (1977); Watson and Steward, *J. Chrom.*, 134, 182 (1977); ibid, 132, 155–159 (1977). Radioimmunoassay has been reported for amitriptyline by Aherne, et al., *Br. J. Clin. Pharmac.*, 3, 561 (1976); Turner, *Lancet*, 1316 (1977); and Aherne et al., *Lancet*, 1214 (1977). In Aherne, et al., ibid, a synthesis for an antigen for antibody formation is described, where nortriptyline is substituted with aminobutylene followed by conjugation to bovine serum albumin employing carbodiimide. In another antigen conjugate synthesis by Kaul, et al., *J. Anal. Tox.*, 1, 236 (1977), nortriptyline was conjugated to bovine serum albumin through a succinic group. The resulting antibodies were found to have significant cross-reactivity with a number of other tricyclic drugs.

U.S. Pat. No. 4,275,160 discloses imipramine derivatives and poly(amino acid) conjugates. U.S. Pat. No. 4,307,245 describes amitriptyline conjugates to antigenic proteins and enzymes. U.S. Pat. No. 4,220,722 discloses a method for conjugating to polyamino compounds employing haloacyl groups and compositions prepared thereby.

SUMMARY OF THE INVENTION

A synthetic procedure is provided for preparing derivatives of desmethylimipramine functionalized at the 10-position for conjugation to proteinaceous materials, particularly antigenic and enzymatic poly(amino acids). The antigenic conjugate is employed for the production of antibodies for use in immunoassays. The enzyme conjugate is employed as a reagent for the determination of desmethylimipramine in immunoassays. The antibodies and enzyme conjugates are provided in combination in kits to be used for the rapid and accurate determination of desmethylimipramine in serum as well as other physiological fluids.

DESCRIPTION OF THE PREFERRED EMBODIMENTS

Novel compounds are provided which are desmethylimipramine derivatives having a linking group at the 10-position to which is conjugated a poly(amino acid), which is antigenic or an enzyme. The antigenic conjugates are employed as an immunogen for the production of antibodies which are specific for desmethylimipramine; the antibodies find use in immunoassays. The enzyme conjugates are employed as a reagent in enzyme assays for the determination of desmethylimipramine.

For the most part, compounds of this invention will have the following formula:

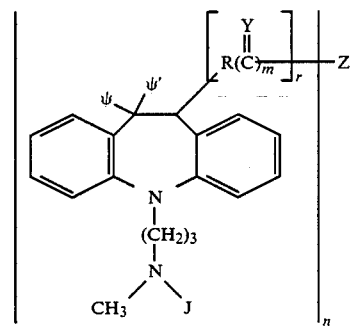

wherein:

$\psi$ and $\psi'$ are hydrogen atoms or are taken together to form a double bond to an oxygen atom (oxo), being hydrogen atoms when Z is poly(amino acid);

Y is chalcogen (oxygen or sulfur atom) or an imino (NH);

J is a hydrogen atom or non-oxo-carbonyl, usually alkoxy-carbonyl or from 2 to 6 carbon atoms, preferably 3 to 4 carbon atoms, which may contain from 1–3 halogen atoms of atomic number 17 to 35, usually chlorine atoms, normally as $\beta$-substituents when three or more carbon atoms are present; being non-oxo-carbonyl when $\psi$ and $\psi'$ are taken together to form oxo;

R is a bond or an aliphatic linking group of from 1 to 18 atoms other than hydrogen atoms, preferably 5 to 15 atoms other than hydrogen atoms, more preferably 7 to 12 atoms other than hydrogen atoms, which may be carbon atoms, nitrogen atoms, and chalcogen (oxygen and sulfur atoms) including a chain of from 1 to 15 atoms, preferably from 3 to 12 atoms, more preferably from 5 to 10 atoms other than hydrogen atoms; usually from 1 to 10, preferably 2 to 6, carbon atoms; usually from 0 to 5, preferably 1 to 3 oxygen atoms present as oxo-carbonyl, non-oxo-carbonyl, or ether, particularly non-oxo-carbonyl; usually from 0 to 3, preferably 1 to 2, nitrogen atoms present as amido, preferably having 1 nitrogen linked to the alicyclic nucleus; and usually from 0 to 2, preferably 1 to 2, sulfur atoms present as thiono or disulfide; wherein for each carbon atom no more than one heteroatom is linked thereto through a saturated bond;

Z is amino; thiol; alkylthio of from 1 to 6 carbon atoms, usually 1 to 3 carbon atoms wherein Z may be taken together with R to give a disulfide; or poly(amino acid) (PAA), which is antigenic or an enzyme; being a hydrogen atom when r is 0 and $\psi$ and $\psi'$ are taken together to form oxo;

m is 0 or 1, usually 0 when Z is thiol or alkylthio or 0 or 1 when Z is PAA;

r is 0 or 1, being 0 when $\psi$ and $\psi'$ are taken together to form oxo, and being otherwise 1;

n is 1 when Z is other than PAA and is otherwise a number on the average between 1 and the molecular weight of Z divided by 500, more usually divided by 1,000 and frequently divided by 1,500, generally ranging from 1 to 500, preferably from 10 to 100, when Z is an antigen, and from 1 to 30, more usually 2 to 20, and preferably from 2 to 16, when Z is an enzyme.

For those compounds where m is 0 and n is 1, the compounds will be of the formula:

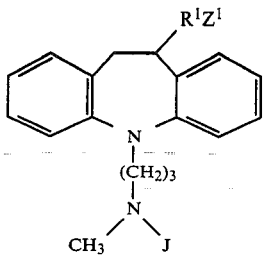 (II)

wherein:

J has been defined previously;

$R^1$ is

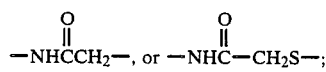

and $Z^1$ is amino, thio of 0 to 6 carbon atoms, including thiol and alkyl thiol of from 1 to 6 carbon atoms, usually 1 to 3 carbon atoms.

When $Z^1$ is thiol, the compounds may be stabilized as a salt, i.e., acetate salt.

When $Z^1$ is a poly(amino acid), preferred compounds will, for the most part, have the formula:

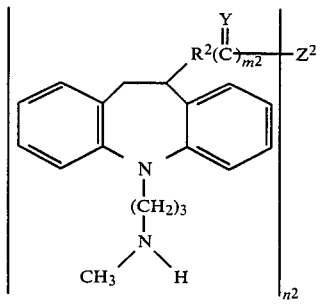 (III)

wherein:

$R^2$ is

M is amino;

Q is C=W, wherein W is an oxygen atom, imino (N—H), or a sulfur atom, particularly an oxygen atom; a is 0 or 1;

T and T' are linking groups of from 1 to 4, preferably 1 to 2, carbon atoms, preferably aliphatic, more preferably alkylene, particularly methylene; when a is 0, T must be at least two carbon atoms;

Y and Y' are, respectively, an oxygen atom, an imino group (N—H), or a sulfur atom, preferably an oxygen atom;

A is a amino;

k is 0 or 1; preferably 1;

p is 0 or 1, preferably 1;

$m^2$ is 0 or 1, preferably 1;

$n^2$ is at least 1, and usually on the average greater than 1, when $Z^2$ is antigenic; $n^2$ will normally be at least 2, and not greater than the molecular weight of $Z^2$ divided by 500, usually not greater than the molecular weight of $Z^2$ divided by 1,000 and preferably not greater than the molecular weight of $Z^2$ divided by 1,500, generally ranging from 2 to 500; when $Z^2$ is an enzyme, $n^2$ will be at least 1, usually not greater than 30, more usually in the range of 2 to 20, and preferably in the range of about 2 to 16.

$Z^2$ is a poly(amino acid) and will generally range from about 5,000 molecular weight, having no upper molecular weight, normally being less than 10,000,000, usually not more than about 600,000. There will usually be different ranges, depending on whether an antigen or an enzyme is involved, with antigens ranging from about 5,000 to $10^7$, usually from about 20,000 to 600,000, and more usually from about 10,000 to 300,000 molecular weight. There will usually be at least about one conjugate group per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugate groups will generally be in the range of from about 2 to 10, usually in the range of 2 to 5.

The preferred compounds of the invention have the following formula:

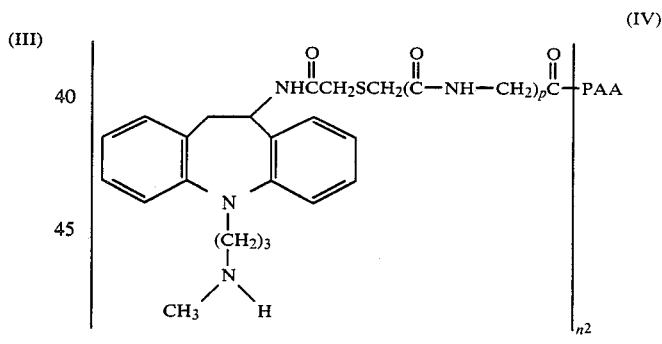 (IV)

wherein:

p and $n^2$ have been defined previously; and

PAA is poly(amino acid) which has been defined previously.

Various protein types may be employed as the antigenic material. These types include albumins, serum proteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the desmethylimipramine is to be measured. Primarily, the enzymes of choice, based on the I.U.B. classification are: Class 1. Oxidoreductases and Class 3. Hyrolases. Particularly in Class 1, the enzymes of interest are dehydrogenases of Class 1.1, more particularly 1.1.1, 1.1.3, and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

The synthetic scheme for preparing the subject compounds is set forth in the following flow chart:

REACTION SEQUENCE I

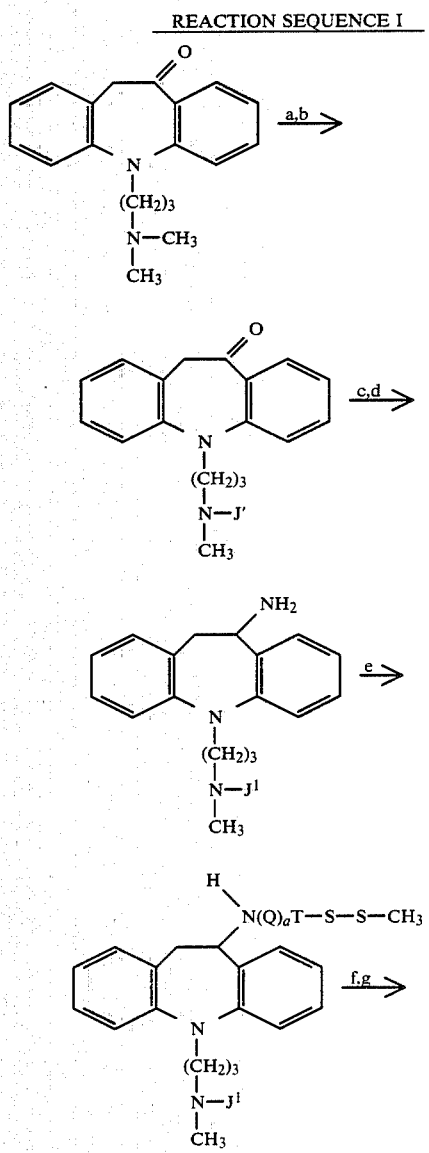

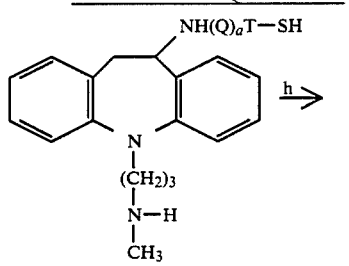

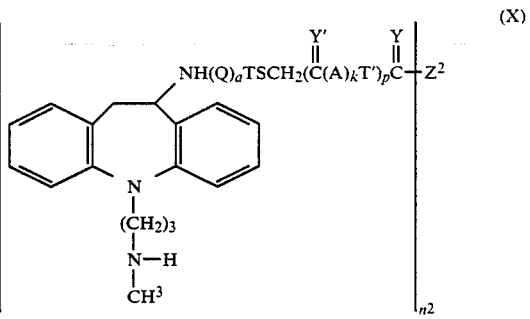

(a) X-J' wherein X is a halogen atom of atomic number 17 to 35 and J' is J except when J is hydrogen atom; preferably trichloroethyl chloroformate;
(b) alkali, usually carbonate;
(c) reducing agent such as cyanoborohydride;
(d) aminating agent such as ammonium acetate;
(e) L(Q)$_a$F' wherein Q and a have been defined previously; L is an ester group for activating non-oxo-carbonyl for linking to an amine group, preferably N-hydroxysuccinimidyl, and F' is a group of from 4 to 10 atoms other than hydrogen in a chain, which atoms are carbon and sulfur wherein at least one carbon atom is linked to non-oxo-carbonyl and sulfur is disulfide; usually F' is —T—S—S—CH$_3$ wherein T has been defined previously; preferably F' is —CH$_2$—S—S—CH$_3$;
(f) reducing agent, usually a metal of atomic number 22 to 30, preferably zinc;
(g) acid, usually acetic acid;
(h)

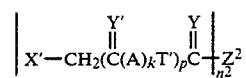

wherein X' is halogen atom of atomic number 17 to 35, preferably bromine and Y, Y', A, T', k, p n$^2$, and Z$^2$ have been defined previously, usually

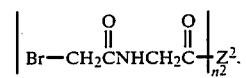

In carrying out the preparation of the compositions of this invention dibenzazepine is converted to V according to the teaching of U.S. Pat. No. 4,275,160 which is incorporated herein by reference. Briefly, dibenzazepine is combined with pyridine and an acyl halide in an anhydrous benzene solution. Halogen, usually bromine, is then added to the acyl derivative of dibenzazepine followed by base elimination which also removes the acyl group. The annular nitrogen is substituted with the 3-dimethylaminopropyl group and the product is then hydrolyzed to introduce an oxo group at C-11.

V is monodemethylated at the non-annular nitrogen by treatment under mild alkaline conditions to give VI. The keto group of VI is converted to an amine group by treatment of VI using an aminating agent in a reductive medium with prolonged heating to give VII. VIII is obtained from VII by mixing VII with N-hydroxy-succinimidyl methyl dithioacetate. VIII is conveniently stored until conversion to IX (which may be stored as a salt, e.g., acetate salt). The protective group of VIII is removed under reductive conditions giving secondary amine IX. Poly(amino acid) conjugates (X) of IX are prepared by combining IX with the appropriate activated poly(amino acid) conjugate.

By employing the above procedure conjugates of desmethylimipramine and poly(amino acids), either antigenic or enzymes may be prepared. The structure of desmethylimipramine is present in the conjugates and those elements of the structure which provide for distinctions between closely similar compounds are exposed to allow for formation of antibodies which are capable of distinguishing desmethylimipramine from similarly structured compounds. The antigenic compounds may be injected into a wide variety of vertebrates in accordance with conventional methods for the production of antibodies. Usually the animals are bled periodically with successive bleeds having improved titer and specificity, then reaching a maximum and diminishing in their specificity and titer. The antibodies prepared in accordance with the present invention bind with I when Z is an antigenic poly(amino acid) or an enzyme and are specific for desmethylimipramine and are able to distinguish between closely related compounds such as imipramine and amitryptiline.

As previously indicated, the antibdies and enzyme reagents prepared in accordance with the subject invention find particular use in immunoassays for the determination of desmethylimipramine. A description of the method for carrying out the immunoassay, which is a homogeneous enzyme immunoassay, may be found in U.S. Pat. No. 3,817,837. The method involves combining the enzyme conjugate, the unknown sample (after treatment to remove metabolites by, e.g., chromatographic separation) suspected of containing desmethylimipramine, and an antibody for desmethylimipramine in an aqueous buffered medium at temperatures in the range of about 10° to 50° C., more usually from about 20° to 40° C., and determining the enzyme activity as compared to the enzyme activity of an assay medium having a known amount of desmethylimipramine.

EXAMPLES

The following examples are offered by way of illustration and not by way of limitation.

All temperatures not otherwise indicated are in centigrade. All parts and percents are by weight except for mixture of liquids which are by volume.
TLC—thin layer chromatography;
GF—gel filtration;
IR—infrared spectroscopy;
CDCl$_3$—deuterted chloroform;
Pmr—proton magnetic resonance spectroscopy;
MHz—megahertz;
TMS—trimethyl silane;
M.S.—mass spectroscopy;
h—hour;

DMF—dimethylformamide;
NHS—N-hydroxysuccinimide;
EDCI—1-ethyl-3-(3-dimethylaminopropyl)carbodiimide;
BSA—bovine serum albumin;
BLG—β-lactoglobulin;
BgG—bovine gamma globulin; and
G-6-PDH—glucose-6-phosphate dehydrogenase.
G-6-P(Na)—sodium glucose-6-phosphate

EXAMPLE 1

Preparation of 5-[3-N-methyl-N-(2,2,2,-trichlorocarboethoxy)amino propyl]-10,11-dihydro-5H-dibenz [b,f] azepinone Into a 200 ml round bottom flask was placed 8.0 g (0.25 mol) of 5-(3-dimethylaminopropyl)-5H-dibenz [b,f] azepin-10-one, (prepared according to the teaching of U.S. Pat. No. 4,275,160, Examples 1–5), 45 ml of anhydrous toluene, 14 g (0.102 mol) of anhydrous potassium carbonate followed 21.7 g (0.102 mol) of 2,2,2-trichloroethyl chloroformate. The solution was stirred vigorously and slowly brought to reflux with an oil bath. Reflux continued for approximately 12 hours.

TLC analysis, silica gel, GF-chloroform showed some carbamate formed after less than one hour's time (visualization with UV lamp and ceric sulfate-H$_2$SO$_4$ spray). The reaction was cooled and added to a separatory funnel containing 200 ml water and was extracted several times with chloroform. The organic phase was again extracted with two 100-ml portions of 10% HCl, 200 ml water, dried over MgSO$_4$, filtered, and concentrated on a rotary vaporator leaving a dark brown oil (~15 g).

Chromatography of the oil was performed on a glass column with dry silica gel 60–200 mesh (J. T. Baker Chemical, Phillipsburg, N. J.) ~650 g, 5×80 cm column dimension. The crude product, dissolved in a small amount of dichloromethane, was placed at the top of the column. Two liters of solvent (dichloromethane) was collected prior to collection of ~20 ml increments on an automatic fraction collector. After faster moving impurities were eluted, larger volume fractions were collected and TLC indicated only one spot corresponding to carbamate. These fractions were combined and concentrated to give 9.8 g of product.

IR: CDCl$_3$ (1670 cm$^{-1}$, aromatic carbonyl); (1720 cm$^{-1}$ carbamate carbonyl stretch)

Pmr: 90MHz(CDCl$_3$—TMS) δ8.1 (dd,1 1H, J~9Hz, J~1.5Hz, 1H aromatic); 7.13 (m, 7H aromatic); 4.64 (br.s, 2H,—OCH$_2$CCl$_3$); 3.96 (s, 2H,—CH$_2$CO—); 3.96 (t,2H,J~6Hz,—N—CH$_2$CH$_2$—); 3.34 (t,2H,J~Hz,—CH$_2$CH$_2$NCH$_3$); 2.85 (s,3H,—NCH$_3$); 1.89 (m,2H,CH$_2$,CH$_2$—CH$_2$)

EXAMPLE 2

Preparation of 5-[3 N-methyl-N-(2,2,2-trichlorocarboethoxy)amino propyl]-10-amino-10,11-dihydro-5H-dibenz [b,f]azepine Into a 100 ml pear-shaped flask equipped with a CaCl$_2$ drying tube and a reflux condenser was placed 3.8 g (0.00835 mol) of the product of Example 1, 6.4 g (0.0835 mol) of anhydrous ammonium acetate (dried in dessicator under vacuum over CaCl$_2$), 50 ml of an anhydrous methanol and 1.5 g (0.0250 mol) of sodium cyanotrihydriodoborate. The mixture was stired and brought to 50°.

After 72 h, an additional 1 g of anhydrous ammonium acetate and 5 gm sodium cyanotrihydridoborate was added.

After 100 h the reaction mixture cooled and was poured into a separatory funnel containing 300 ml water and was extracted with three 100-ml portions of chloroform. The organic phases were combined, dried with $MgSO_4$, filtered and concentrated on a rotary vaporator.

One-half of the material was applied to twelve 20×20 cm preparative plates, 2.5 mm silica gel 60 PF-254+366 (Analtech). The plates were treated with ethyl ether 3 times. Material was then extracted from the absorbant with 10% methanol-90% dichloromethane and concentrated. This material was re-subjected to the above chromatographic condition, but ethyl ether saturated with ammonia gas was substituted for the ethyl ether and the plates were treated only one time. (The major band was collected after UV light inspection indicated the presence of the desired material.) These two chromatographic steps gave pure product which was isolated in 60–70% yield.

IR: $CHCl_3$ (1720 $cm^{-1}$, carbamylcarbonyl); (3380–3350 $cm^{-1}$, NH stretching modes)

Pmr: 90MHz ($CDCl_3$—TMS) $\delta$7.07 (m,8H,aromatic); 5.64 (S,2H,O—$CH_2CCl_3$); 4.48 (m,1H,—$NH_2$—CH—$CH_2$); 3.75 (t,2H,J~6Hz,N—$\underline{CH_2}$—$CH_2$); 3.34 (t,2H,J~6Hz; 2.85 (s,3H,—$NCH_3$); 2.13 (br.s,2H,$NH_2$)

EXAMPLE 3

Preparation of
N-hydroxysuccinimidylmethyldithioacetic acid

Into a 50 ml round bottom flask was placed 1.2 g (8.86 mmols) of methyl dithioacetic acid (prepared according to P. Singh, et al. (1979) *Anal. Biochemistry* 104, 51) 35 ml of dichloromethane, and 1.09 g (9.54 mmols) of NHS (crystallized from ethyl acetate). The solution was cooled in an ice bath before addition of 1.96 g (9.54 mmols) of distilled N,N'-dicyclohexylcarbodiimide; a mild exothermic reaction occurred. After stirring for 4 h, the solution was filtered through a medium sintered glass funnel, precipitated urea was washed with dichloromethane and light brown filtrate concentrated on a rotary evaporation at ambient temperature.

This material was dissolved in 10 ml $CH_2Cl_2$ and applied to the top of a 2.5×43 cm dry glass column packed with 110 g of silanized silica gel 60 particle size 0.063–0.200 mm (70–230 mesh ASTM, E Merck).

The eluant was 1/1—$CH_2Cl_2$/hexane. The fractions were monitored by tlc on silanized silica gel RP-2 (E. Merck) with 1/1-$CH_2Cl_2$/hexane as the eluant.

Fractions 22–40 were combined (dry weight 1.2 g, approx. 60% yield). The dry material was dissolved in $CH_2Cl_2$/hexane solution and cooled overnight at 0°. More hexane was added as needed to promote crystallization (900 g white NHS ester, m.p. 79°–81°).

Microanalysis sulfur calc. 27.25%; Act. 27.24%.

EXAMPLE 4

Preparation of
5-(3-N-methyl-N-(2,2,2-trichlorocarboethoxy)aminopropyl)-10,11-dihydro-10-methyldithioacetamido-5H-dibenz [b,f] azepine A solution of 557 mg (1.22 mmols) of 5-[3-N-methyl-N-(2,2,2-trichlorocarboethoxy)amino propyl]-10-amino-10,11-dihydro-5H-dibenz [b,f] azepine from Example 2, 287 mg (1.22 mmols) of N-hydroxysuccinimidyl methyl dithioacetate from Example 3 and 25 ml of anhydrous tetrahydrofuran was stirred at ambient temperatures for 4 h.

TLC analysis was conducted on silanized silica gel RP-2 eluant 20% hexane-80% dichloromethane; comparison with N-hydroxysuccinimidyl methyldithioacetate, N-hydroxysuccinimide and starting amine revealed that the reaction was complete. (Rf value of product ~0.13.)

The reaction mixture was concentrated and dissolved in 20% hexane-80% $CH_2CL_2$ and placed at the top of a glass column 2.5×42 cm dry packed with 130 gm of silica gel 60, silanized particle size 0.063–0.20 mm (70–230 mesh ASTM) RP-2. The eluant was 20% hexane-80% dichloromethane and 15–20 ml fractions were collected (approximately 96% yield).

IR: 1% in KBr (1650 $cm^{-1}$ amide carbonyl); (1740 $cm^{-1}$ carbamate carbonyl)

Pmr: 90 MHz ($CDCl_3$—TMS) $\delta$2.4 (s,3H,$SCH_3$); 2.88 (br.s,3H,—$NCH_3$) 3.38 (s,2H,—$COCH_2S$—); 4.68 (br.s,2H,—O—$CH_2CCl_3$); 5.62 (br.m, 1H,—CH-NHCO—)

EXAMPLE 5

Preparation of
5-(3-N-methylaminopropyl)-10,11-dihydro-10-thioacetamido-5H-dibenz [b,f] azepine Into a 25 ml round bottom flask equipped with stopper was placed 140 mg (0.243 mmol) of the product of Example 4, excess zinc dust (>70 mg), 10 ml of glacial acetic acid. The mixture was stirred at ambient temperatures for 24 h (a white precipitate of $ZnCl_2$ formed). Reaction progress was monitored by TLC on RP-2silanized silica gel plates with 15% methanol-85% dichloromethane as the eluant (the plates were observed under UV lamp and with Ellman's reagent spray.

The reaction mixture was filtered to remove solids, was washed with acetic acid-methanol, and was concentrated on a rotary vaporator under high vacuum without heating. The residue was taken up in water/chloroform extracted with many portions of chloroform dried with $MgSO_4$, filtered, and concentrated. This material was applied to one preparative TLC 20×20 cm plate, 2.5 mm thickness, silanized silica gel PF 254 (E. Merck). The plate was eluted with 15% methanol-85% dichloromethane. The band corresponding to the desired product was isolated. The product was extracted from the above solvent with 20/80 methanol/dichloromethane, concentrated on rotary evaporator and under high vacuum giving a light yellow foam, 60 mg, 70% yield. Rf value ~0.62 sulfhydryl 85% $CH_2Cl_2$-15% methanol.

IR: $CHCl_3$ film (1650 $cm^{-1}$ amide carbonyl); (acetate salt —$NH_2^+CH_3AcO^-$, 1720 $cm^{-1}$ $CO_2$—)

PMR: 90MHz ($CD_3OD/CDCl_3$-TMS) $\delta$7.1 (m,8H, aromatic); $\delta$5.54 (m,1H,—CH—NCO—); 3.87(t,2H,J~6Hz,N—$\underline{CH_2}CH_2$—); 3.23 (s,—$\underline{CH_2}SH$); 3.05 (t,2H,J~6Hz,—$CH_2CH_2$—$NHCH_3$); 2.60 (s,3H,$NCH_3$) 2.04 (m,2H,—$\underline{CH_2}CH_2$—$NHCH_3$)

EXAMPLE 6

Preparation of the Conjugate of BSA-bromoacetylglycine with 5-(3-N-methylaminopropyl)-10,11-dihydro-10-thioacetamido-5H-dibenz[b,f]azepine a. Preparation of the NHS succinimic ester of bromoacetylglycine

To a solution of bromoacetylglycine (1 g, m.p. 114°–115°) in 10 ml of DMF was added powdered N-hydroxysuccinimide (1 g) and EDCI (1 g, 5.2 mmole) under nitrogen at 0°. The resulting clear solution was then allowed to stir at 5° after 18 h and was used directly without the isolation of the NHS ester.

b. Preparation of the conjugate of bromoacetylglycine and BSA

To a clear solution of BSA (1.5 g) in phosphate buffer (pH 9.0, 0.05 M, 100 ml) and DMF (6 ml) was added dropwise the NHS ester of bromoacetylglycine (500 mg) prepared in (a) above, in 6 ml DMF at 0° for a period of 30 min. Before the addition of the NHS ester, the pH of the BSA solution was about 8.0. After the addition of the NHS ester, the pH dropped to 5–6, the pH (5.86) of the reaction mixture was adjusted to 6.8 and the mixture was stirred overnight at 5°. The resulting conjugate was then dialyzed against 3×4 liter phosphate buffer (0.0125 M, pH 6.8) and 2×4 liter phosphate buffer (0.05 M, pH 6.8). The conjugate was diluted to 150 ml and stored for further conjugation. The concentraction of this protein conjugate was determined by UV and found to be 8.8 mg protein/ml solution.

c. Conjugation of BSA-bromoacetylglycine and 5-(3-N-methylaminopropyl)-10,11-dihydro-10-thioacetamido-5H-dibenz[b,f]azepine Fifty ml of the BSA-bromoacetylglycine solution from (b) above (~0.375 g) was placed in a 125 ml flask followed by 10 ml of 0.4M $Na_2HPO_4$-$NaH_2PO_4$ buffer pH 7.25 (pH of protein solution 7.21 by pH meter).

The solution was cooled in an ice bath at 4°; then 100 mg of the mercaptoacetamido product of Example 5 was dissolved in 1 ml of DMF and was added slowly dropwise to the stirring protein solution. An additional 2 ml of DMF was used to rinse residual material. After the addition was complete, the protein solution appeared considerably turbid.

The above solution was stirred in a cold room (4°) for 3 days.

The above solution was placed in a semi-permeable membrane (cylinder diameter 20.4 mm, M.W. cut off 6,000–8,000) and dialyzed against deionized water pH 9.8 with $NH_4OH$, 4 liters, 3 times for 8 h each.

The material was then chromatographed using Sephadex G-50 medium with a bed volume of four times the volume of the product solution. Fractions of approximately 15 ml each were collected, UV of fractions was recorded on a Carey 15 spectrophotometer. The appropriate fractions were combined based on the UV data. The combined fractions were lyophilized to give 0.440 g of product with a hapten number of 24.

EXAMPLE 7

Preparation of the Conjugate of BgG-bromoacetylglycine with 5-(3-N-methylaminopropyl)-10,11-dihydro-10-thioacetamido-5H-dibenz[b,f]azepine a. Conjugation of bromoacetylglycine to BgG

To a clear solution of BgG (1.5 g) in a mixture of phosphate buffer (100 ml, pH 9, 0.05 M) and DMF (5 ml) was added dropwise the NHS ester of bromoacetylglycine (500 mg in 6 ml DMF, prepared as in Example 6a above, at 0° for a period of 30 min. The pH of the BgG solution before the addition of NHS solution was 8. The pH dropped to 6.3 after addition of the NHS solution; the pH was then adjusted to 6.8. The resulting mixture was allowed to stir overnight at 5°. After 18 hours, the conjugate was dialyzed against 4×4 liter phosphate buffer (0.0125 M, pH 6.8) 2×4 liter (0.05 M, pH 6.8). The conjugate was diluted to 150 ml and stored for further conjugation. The concentration of this protein conjugate was determined by UV and found to be 9.58 mg/ml.

b. Conjugation of BgG-bromoacetylglycine and 5-(3-N-methylaminopropyl)-10,11-dihydro-10-thioacetamido-5H-dibenz[b,f]azepine Fifty ml of the BgG-bromoacetylglycine solution from (a) above (~0.375 g) was placed in a 125 ml flask and 10 ml of 0.4M $Na_2HPO_4$-$NaH_2PO_4$ buffer pH 7.23 was added. The mixture was then cooled to 4° in an ice bath. Next, was added 100 mg (0.281 mmol) of 5-(3-N-methylaminopropyl)-10,11-dihydro-10-thioacetamido-5H-dibenz[b,f]azepine from Example 5 dissolved in 1 ml of DMF. The solution became turbid then very milky. An additional 2 ml of DMF used to rinse the remaining material into the reaction vessel.

The above solution was stirred in a cold room (4°) for 3 days.

The above solution was placed in a semi-permeable membrane tubing (cylinder diameter 20.4 mm, M.W. cut off 6,000–8,000) and dialyzed against deionized water pH 9.8 with $NH_4OH$, 4 liters, 3 times for 8 h each.

The material was then chromatographed using Sephadex G-50 medium with a bed volume of four times the volume of the product solution. Fractions of approximately 15 ml each were collected, UV of fractions was recorded on Carey 15 spectrophotometer. The appropriate fractions were combined based on the UV data. The combined fractions were lyophilized to give 0.440 g of product with a hapten number of 8.

EXAMPLE 8

Preparation of the Conjugate of G-6-PDH and 5-(3-N-methylaminopropyl)-10,11-dihydro-10-thioacetamido-5H-dibenz[b,f]azepine a. Preparation of the conjugate of bromoacetyl glycine and G-6-PDH

G-6-PDH (61 mg in 8 ml of 0.055 M Tris buffer at pH 8.0) was brought to 4° and 320 mg each G-G-P ($Na_2$) salt and NADH were added and dissolved. To this solution, a 0.5 M bromoacetylglycyl NHS ester in DMF, prepared as in Example 6a above, was added until the ester to enzyme ratio was 3:1 and the deactivation of the enzyme was 65%. The solution was dialysed against Tris buffer (0.055 M, pH 8.0) 4000 ml for 18 h.

b. Conjugation of 5-(3-N-methylaminopropyl) 10,11-dihydro-10-thioacetamido-5H-dibenz[b,f]azepine to bromoacetylglycyl G-6-PDH The hapten material (63 mg) from Example 5 was reconstituted in 1.5 ml of DMF. All of the dialysed material from Example 8a was placed in a side arm flask and cooled to 4°. The hapten was added dropwise until the inhibition against anti-DMI antibodies was 45–50% (a hapten to enzyme ratio of about 95). The G-6-PDH conjugate was then desalted at 4° over a G50 column with Tris buffer (0.055 M, pH 8.0) with preservatives.

EXAMPLE 9

Assay for Desmethylimipramine

In order to demonstrate the efficacy of compounds prepared in accordance with the subject invention, the antibodies and the enzyme conjugate were employed in a number of assays for desmethylimipramine. In carrying out the assay, a Gilford Stasar III ® microsample spectrophotometer was employed with a Thermocuvette (3017T) with a flow cell. All readings were made at 340 nm. The following solutions were prepared as reagents for use in the assay.

Buffer:
 0.055 M tris-HCl pH 8.1 (RT)
Enzyme Conjugate
 Buffer
 0.9% NaCl
 1.0% BLG, pH 8.1 (RT)
Sufficient enzyme conjugate (from Example 8) to give a maximum rate of ΔOD equal to 800–1000 in the assay medium
Assay buffer;
 Buffer
 0.5% NaCl
 0.01% (v/v) Triton X-100, pH 8.1(RT)
Antibody Reagent:
 Buffer
 0.1% BLG,
 G-6-P(Na) 0.22 M,
 NAD 0.13 M, pH 5(RT).
Antidesmethylimipramine optimized for assay (antibodies prepared in sheep using the conjugate of Example 7)

(All % indicated are w/v g/ml.)

The protocol employed for carrying out an assay was as follows:

The sample was treated first to remove metabolites. A 100 mg column (C-2 from Analytichem, Harbor City, California) was washed with approximately one ml of methanol followed by aproximately one ml of water. The sample (500 μl) was placed on the top of the column. A vacuum apparatus was attached to the bottom and a vacuum was drawn on the column. The eluate obtained was discarded and the column was washed with 900 μl of a solution which was 70% 0.1 M sodium acetate, pH 4.2, 30% acetonitrile, and 5 mM heptane sulfonate. A vacuum was again drawn on the column and the eluate was discarded. Next, the column was contacted with 500 μl of a solution which was 50% acetonitrile, 25% methanol, and 25% 5 mM K₂HPO₄, pH 7. The eluant was collected and used in the assay procedure.

Into a diluter was drawn 15 microliters (μl) of the above eluant. This sample was dispensed with 250 microliters of the assay buffer into a one milliliter Croan cup. Into the Croan cup was introduced 15 μl of the antibody reagent with 250 μl of the assay buffer, followed by the addition of 15 μl of the enzyme reagent and 250 μl of the assay buffer. Immediately after the enzyme addition, the entire sample was aspirated into the flow cell. After 10 seconds, a first reading is taken, followed by a second reading, after a 50 second interval. The results are reported as the difference in absorbance ×2.667.

| Sample Concentration of Desmethylimipramine (ng/ml) | ΔOD |
|---|---|
| 0 | 702 |
| 50 | 737 |
| 100 | 765 |
| 200 | 800 |
| 350 | 834 |
| 500 | 854 |

*lowest rate in assay with predetermined amount of antibody.
**rate of enzyme in absence of antibody.

The subject assay provides for a sensitive accurate method for determining desmethylimipramine in biological fluids such as serum. The subject invention provides reagents specific for desmethylimipramine, which allows for a substantial range of changes in enzyme activity with change in concentration of desmethylimipramine. The method is rapid, the protocol is simple and relatively free of technician introduced error.

Although the foregoing invention has been described in some detail by way of illustration and example for purposes of clarity and understanding, it will be obvious that certain changes and modifications may be practiced within the scope of the appended claims.

What is claimed is:

1. A compound of the structure

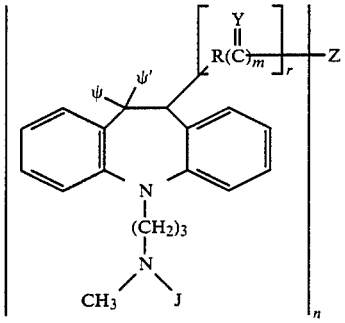

wherein:
- ψ and ψ' are hydrogen atoms or are taken together to form a double bond to an oxygen atom (oxo) when J is other than a hydrogen atom, being a hydrogen atom when Z is poly(amino acid);
- Y is a chalcogen (oxygen or sulfur atom) or an imino group;
- J is a hydrogen atom, or non-oxo-carbonyl, being non-oxo-carbonyl when ψ and ψ' are taken together to form oxo;
- R is a bond or an aliphatic linking group of from 1 to 18 atoms other than hydrogen atoms comprising carbon, nitrogen, and chalcogen (oxygen and sulfur atoms);
- Z is an amino group; thiol; thio substituted with alkyl of from 1 to 6 carbon atoms; or poly(amino acid);

being a hydrogen atom when r is 0 and ψ and ψ' are taken together to form oxo;

m is 0 or 1;

r is 0 or 1, being 0 when ψ and ψ' are taken together to form oxo, and being otherwise 1;

n is 1 when Z is other than poly(amino aid) and is otherwise a number on the average between 1 and the molecular weight of Z divided by 500.

2. The compound of claim 1 wherein ψ and ψ' are taken together to form oxo, r is 0, Z is a hydrogen atom, and J is non-oxo-carbonyl.

3. The compound of claim 1 wherein ψ and ψ' are hydrogen atoms, r is 0, Z is amino, and J is non-oxo-carbonyl.

4. A compound of the formula:

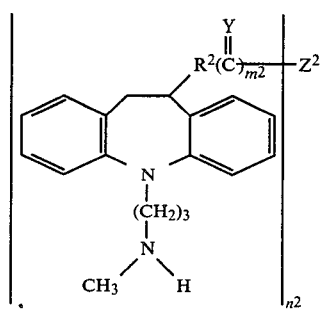

wherein:
R² is

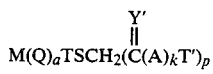

M is amino;

Q is C=W wherein W is an oxygen atom, an imino group, or a sulfur atom;

T and T' are linking groups of from 1 to 4 carbon atoms;

Y and Y' are, respectively an oxygen atom, an imino group, or a sulfur atom;

A is an amino group or an oxygen atom;

a, k, p, and m² are, respectively, 0 or 1;

n² is at least 1 and on the average not greater than the molecular weight of Z² divided by 500; and Z² is poly(amino acid).

5. The compound of claim 4 wherein R² is

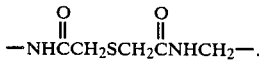

6. The compound of claim 4 wherein Z² is an antigen.

7. The compound of claim 4 wherein Z² is an bovine serum albumin.

8. The compound of claim 4 wherein Z² is bovine gamma globulin.

9. The compound of claim 4 wherein Z² is an enzyme.

10. The compound of claim 4 wherein Z² is glucose-6-phosphate dehydrogenase.

11. Antibodies produced in response to the compound of claim 4 wherein Z² is an antigen, which antibodies bind to the compound of claim 4 wherein Z² is an antigen, the compound of claim 4 wherein Z² is an enzyme and desmethylimipramine.

12. A compound of the formula:

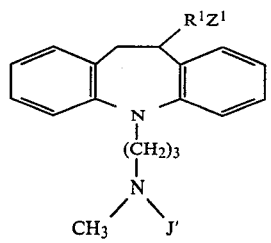

wherein:
J' is a hydrogen atom or non-oxo-carbonyl,
R₁¹ is amino

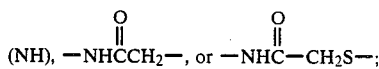

Z is a hydrogen atom or thiol of 0 to 6 carbon atoms.

13. A compound of the formula:

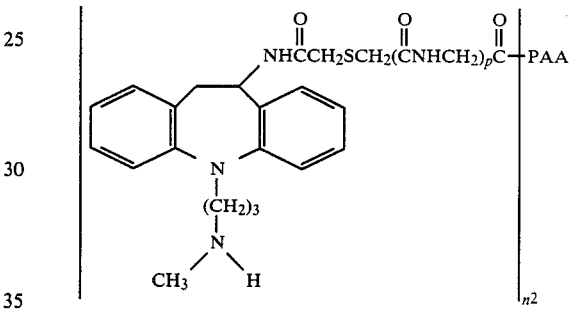

wherein:
P is 0 or 1;
n² is at least 1 and on the average not greater than the molecular weight of PAA divided by 500; and
PAA is a poly(amino acid) antigen or enzyme.

14. Antibodies produced in response to the compound of claim 13 which bind to the compound of claim 13 and to desmethylimipramine.

15. The compound of claim 13 wherein PAA is bovine serum albumin.

16. The compound of claim 13 wherein PAA is bovine gamma globulin.

17. The compound of claim 13 wherein PAA is glucose-6-phosphate dehydrogenase.

18. A method for determining the presence of desmethylimipramine in a sample suspected of containing desmethylimipramine, which comprises:

(a) combining the sample in an aqueous medium with (1) an antibody produced in response to the compound of claim 4, wherein Z² is an antigen and (2) the compound of claim 4 wherein Z² is an enzyme, (b) determining the enzyme activity of the combination, and (c) determining the presence of desmethylimipramine in the sample by comparing the enzyme activity with the enzyme activity of an assay medium having a known amount of desmethylimipramine.

19. In an enzyme immunoassay method for determining desmethylimipramine, the improvement which comprises employing (1) an antibody produced in response to the compound of claim 4 wherein Z² is an antigen and (2) the compound of claim 4 wherein Z² is an enzyme.

* * * * *